United States Patent
Mithiue et al.

(10) Patent No.: US 7,048,718 B1
(45) Date of Patent: May 23, 2006

(54) WINGED INJECTION NEEDLE HAVING NEEDLE COVERING MEANS

(75) Inventors: Tetutoshi Mithiue, Hirosima (JP); Shyouiti Fujii, Izumo (JP); Takashi Doi, Izumo (JP); Takeshi Okamoto, Izumo (JP)

(73) Assignee: JMS Co., LTD, Hiroshima (JP)

( * ) Notice: Subject to any disclaimer, the term of this patent is extended or adjusted under 35 U.S.C. 154(b) by 513 days.

(21) Appl. No.: 10/089,325

(22) PCT Filed: Sep. 27, 2000

(86) PCT No.: PCT/JP00/06633

§ 371 (c)(1),
(2), (4) Date: Jul. 12, 2002

(87) PCT Pub. No.: WO01/23021

PCT Pub. Date: Apr. 5, 2001

(30) Foreign Application Priority Data

Sep. 27, 1999 (JP) .................................. 11-272845
Mar. 17, 2000 (JP) .............................. 2000-077314

(51) Int. Cl.
*A61M 5/00* (2006.01)
*A61M 5/178* (2006.01)

(52) U.S. Cl. .................................. 604/171; 604/164.04
(58) Field of Classification Search ................ 604/110, 604/165.03, 171, 177, 164.07, 163, 192, 604/158, 263, 264
See application file for complete search history.

(56) References Cited

U.S. PATENT DOCUMENTS

| | | | |
|---|---|---|---|
| 3,595,230 A * | 7/1971 | Suyeoka et al. ............. 604/192 |
| 4,198,973 A | 4/1980 | Millet |
| 4,627,841 A | 12/1986 | Dorr |
| 4,888,001 A * | 12/1989 | Schoenberg ................. 604/162 |
| 5,112,311 A | 5/1992 | Utterberg et al. |
| 5,147,319 A | 9/1992 | Ishikawa et al. |
| 5,197,956 A | 3/1993 | Brizuela |
| 5,266,072 A | 11/1993 | Utterberg et al. |
| 5,382,240 A | 1/1995 | Lam |
| 5,433,703 A | 7/1995 | Utterberg et al. |
| 5,833,670 A * | 11/1998 | Dillon et al. ................ 604/263 |

FOREIGN PATENT DOCUMENTS

DE 197 38 558 3/1999

(Continued)

*Primary Examiner*—Nicholas D. Lucchesi
*Assistant Examiner*—Matthew F. DeSanto
(74) *Attorney, Agent, or Firm*—D. Peter Hochberg; Katherine R. Vieyra; William H. Holt (57) ABSTRACT

A winged injection needle having a needle covering means used at treatments for infusion solution, blood transfusion and extracorporeal blood circulation, characterized by comprising a puncturing needle tube (206), a hub (208) for holding the base end of the needle tube, and a hollow needle housing member for permitting the hub to displace by sliding and to be housed in the entirely in its lumen, and by being provided with an erroneous puncturing prevention means satisfying the following three conditions: (1) the injection noodle can be easily and safety housed after use, (2) its construction is simple and easy to handle to permit easy production at low costs, and (3) it can be safely disposed of.

13 Claims, 9 Drawing Sheets

FOREIGN PATENT DOCUMENTS

| | | |
|---|---|---|
| JP | 56-30944 | 3/1981 |
| JP | 01-212561 | 8/1989 |
| JP | 01-170249 | 12/1989 |
| JP | 4-36026 | 6/1992 |
| JP | 04-180772 | 6/1992 |
| JP | 04-261665 | 9/1992 |
| JP | 06-007442 | 1/1994 |
| JP | 06-225939 | 8/1994 |
| JP | 07-075671 | 3/1995 |
| JP | 08-206195 | 8/1996 |
| JP | 2535342 | 9/1996 |
| WO | WO 91/04761 | 4/1991 |

\* cited by examiner

WINGED INJECTION NEEDLE HAVING NEEDLE COVERING MEANS

BACKGROUND OF THE INVENTION

1. Field of the Invention

The present invention relates to a winged injection needle having needle covering means, comprising at least a needle tube for puncturing, a spherical hub for holding the base end of the needle tube, a hollow needle-housing member for allowing the hub to be displaced by sliding and allowing the entirety of the needle tube for puncturing and the hub to be housed within the lumen of the needle-housing member by the displacement, a pair of flexible wings projectingly formed on left and right outer faces of the hollow needle-housing member, and a guide tube connected to the hub.

2. Description of the Prior Art (1) Conventionally, in medical institutions contamination and infection caused by erroneous puncture of an injection needle, a puncture needle, etc. have been problems and, in particular, since there has been increasing social concern about hepatitis, AIDS, etc. in recent years, attention is being given to means for actively preventing accidents such as erroneous puncture. However, since the medical institutions are also being urged to cut medical costs, the means and methods for preventing contamination and infection have not been developed as was expected.

In the past, various covers and means have been devised for making it difficult to cause an erroneous puncture when housing an injection needle or a puncture needle after use. Although they include not only covers for winged injection needles but also those for simple injection needles, the present invention discloses covering means for a winged injection needle, which is often used for treatment involving infusion, blood transfusion or extracorporeal blood circulation.

(2) Much publicly-known technology has been disclosed regarding means for safely housing a winged injection needle after use, and it is mainly those having a simple constitution that will be exemplified.

The winged injection needle is formed from an injection needle, a needle base to which the needle is fixed, and a guide tube that is connected to the needle base, and many of the erroneous puncture prevention means are constructed so that the injection needle and the needle base can move relative to each other so as to prevent an erroneous puncture after use.

Conventionally known winged injection needles can be broadly classified into two types; those in which the wing is attached to the injection needle or the needle base, and those in which the wing is attached to a cover.

(a) Examples of the former are disclosed in JP, B, 6-7861, JP, A, 8-206195, JP, B, 4-36026, JP, A, 4-261665, JU, B, 5-22182, etc.

(b) Examples of the latter are disclosed in JP, B, 6-7861 (both types are disclosed), JP, B, 2535342, etc.

However, the above-mentioned disclosed means for preventing erroneous puncture are not completely satisfactory from an overall viewpoint, which includes operability, safety, simple structure, cost reduction and hygienic disposal after use.

A winged needle disclosed in JP, B, 6-7861, in which a wing is formed on a protector, has a simple mechanism and is more advantageous in comparison with other erroneous puncture prevention instruments. However, since this erroneous puncture prevention instrument has some defects as described below, attempts have been made to improve it.

That is to say, in the above-mentioned example, it is necessary to form a protrusion and a recess on both a hub and the protector in order to reliably regulate the position of the needle at an exposed position and a housed position, and positioning and adjustment of the dimensions need to be devised. Furthermore, in order for there to be easy and reliable latching when using and housing the puncture needle, it is desirable that engaging means is formed on the entire outer surface of the hub or the entire lumen of the protector, but this makes the structure complicated and increases the production cost. Furthermore, since a tightly-fitting structure is provided so that the needle hub does not move easily within the protector when puncturing and when housing, there is the defect that it is difficult to move the protector smoothly when sliding it.

Furthermore, for many of the conventional winged injection needles disclosed in JP, B, 6-7861, etc. there is the possibility that, when disposing of an injection needle after use, the liquid drug preparation or blood remaining in the needle or tube might leak and contaminate the operator's hand. That is to say, there is the problem that they cannot be disposed of safely.

OBJECT OF THE INVENTION

An object of the present invention is to eliminate the above-mentioned problems of the prior art and provide a winged injection needle equipped with erroneous puncture prevention means that satisfies at least the following three conditions:

(1) it allows the injection needle to be more safely and easily housed after use;

(2) it has a simple structure, ease of handling, and ease of production at low cost; and (3) it can be safely disposed of.

SUMMARY OF INVENTION

A first aspect of the present invention is a winged injection needle that includes at least a needle tube (A) for puncturing, a spherical hub (B) for retaining the base end of the needle tube, a hollow needle-housing member (C) allowing the hub (B) to be displaced by sliding within the lumen of the needle-housing member (C) and allowing the entirety of the needle tube for puncturing and the hub to be housed within the lumen by the displacement, a pair of flexible wings (D) projectingly formed on the left and right outer faces of the hollow needle-housing member (C), and a guide tube (E) joined to the hub (B), wherein the hub (B) includes, on a cross section in the axial direction of the needle, a middle part formed so as to have a maximum diameter and two side parts formed so as to have a smaller diameter than the middle part, the flexible wings are provided on the outer face of the needle-housing member (C), at least the lumen of the needle-housing member has flexibility, and the lumen of the needle-housing member (C) is provided with at least two enlargement-constriction units, the units being formed alternately from an increased diameter part and a reduced diameter part (hereinafter, this type of winged injection needle is also called a first type of winged injection needle).

A second aspect of the present invention is a winged injection needle according to the above-mentioned first aspect wherein the cross section of the hub (B) in the axial direction of the needle is substantially elliptical.

A third aspect of the present invention is a winged injection needle according to the above-mentioned first or second aspect wherein the needle-housing member (C) is provided with three reduced diameter parts and two increased diameter parts.

A fourth aspect of the present invention is a winged injection needle according to the above-mentioned third aspect wherein, among the three reduced diameter parts, the inner diameter of the reduced diameter part in the middle is smaller than the maximum minor diameter of the elliptical cross section of the hub.

A fifth aspect of the present invention is a winged injection needle according to the above-mentioned third or fourth aspect wherein, among the three reduced diameter parts, the inner diameter of the reduced diameter part in the middle is larger than either of the inner diameters of the reduced diameter part on the forward end side and the reduced diameter part on the base end side.

A sixth aspect of the present invention is a winged injection needle according to any one of the above-mentioned third to fifth aspect wherein the inner diameter of the reduced diameter part on the base end side is smaller than that of the reduced diameter part in the middle and is larger than that of the reduced diameter part on the forward end side.

A seventh aspect of the present invention is a winged injection needle according to any one of the above-mentioned first to sixth aspects wherein, among the above-mentioned two increased diameter parts, the maximum inner diameter of the increased diameter part on the forward end side is smaller than the maximum inner diameter of the increased diameter part on the base end side.

An eighth aspect of the present invention is a winged injection needle according to any one of the above-mentioned first to sixth aspects wherein the wings are formed on the outer face of the increased diameter part on the forward end side.

A ninth aspect of the present invention is a winged injection needle according to any one of the above-mentioned third to eighth aspects wherein non-return means is formed in the reduced diameter part in the middle.

A tenth aspect of the present invention is a winged injection needle that includes at least a needle tube (a) for puncturing, a hub (b) for retaining the base end of the needle tube, a hollow needle-housing member (c) allowing the hub (b) to be displaced by sliding within the lumen of the needle-housing member (c) and allowing the entirety of the needle tube for puncturing and the hub to be housed within the lumen by the displacement, a pair of flexible wings (d) projectingly formed on the left and right outer faces of the hollow needle-housing member (c), and a guide tube (e) joined to the hub (b), wherein the hollow needle-housing member (c) is provided with at least two expanded parts (f) spaced via a reduced diameter part, the expanded parts (f) being expanded radially outward and allowing at least one part of the upper part of the hub (b) to be housed therein (hereinafter, this type of winged injection needle is also called a second type of winged injection needle).

An eleventh aspect of the present invention is a winged injection needle according to the tenth aspect wherein the shape of the reduced diameter part within the lumen of the hollow needle-housing member (c) and the shape of the hub (b) are shapes that allow the hub (b) to be displaced by sliding within the lumen of the hollow needle-housing member (c).

A twelfth aspect of the present invention is a winged injection needle according to the above-mentioned tenth or eleventh aspect wherein the hollow needle-housing member (c) is formed from a flexible material.

A thirteenth aspect of the present invention is a winged injection needle according to any one of the above-mentioned tenth to twelfth aspects wherein the hub (b) is formed so as to have loan arced curved shape in the axial direction in which its upper part is formed from a middle part (i) formed so as to have a maximum diameter in the axial direction and two side parts (ii) formed so that their diameters gradually reduce from the maximum diameter.

A fourteenth aspect of the present invention is a winged injection needle according to any one of the above-mentioned tenth to thirteenth aspects wherein it has a structure such that, when the middle part of the hub (b) is housed in the expanded part, it requires a greater force to move the position of the hub than when the middle part of the hub is housed in the reduced diameter part.

A fifteenth aspect of the present invention is a winged injection needle according to any one of the above-mentioned tenth to fourteenth aspects wherein both side faces of the hub (b) have a straight shape.

A sixteenth aspect of the present invention is a winged injection needle according to any one of the above-mentioned tenth to fifteenth aspects wherein two of the expanded parts (f) are provided in the vicinity of the forward end and in the vicinity of the terminus of the hollow needle-housing member (c).

A seventeenth aspect of the present invention is a winged injection needle according to any one of the above-mentioned tenth to sixteenth aspects wherein the expanded parts (f) have a shape that can house substantially the entire upper part of the hub (b).

An eighteenth aspect of the present invention is a winged injection needle according to any one of the above-mentioned first to seventeenth aspects wherein the pair of flexible wings and the needle-housing member are formed by molding as one piece using a flexible resin.

A nineteenth aspect of the present invention is a winged injection needle according to any one of the above-mentioned first to eighteenth aspects wherein the pair of flexible wings can be folded upward and have a flexibility and a length that are sufficient to cover the needle-housing member, and have an immovable attachment member that allows the wings to be immovably attached to each other after covering the needle-housing member.

A twentieth aspect of the present invention is a winged injection needle according to any one of the above-mentioned first to nineteenth aspects wherein the needle-housing member has on its rear end a liquid drip prevention mechanism.

A twenty-first aspect of the present invention is a winged injection needle according to the above-mentioned twentieth aspect wherein the liquid drip prevention mechanism is a slit provided in the rear end of the needle-housing member.

A twenty-second aspect of the present invention is a winged injection needle according to the above-mentioned twentieth or twenty-first aspect wherein the liquid drip prevention mechanism is a member that is separately provided on the rear end of the needle-housing member and is capable of clamping the guide tube.

A twenty-third aspect of the present invention is a winged injection needle according to the above-mentioned twenty-second aspect wherein the member capable of clamping the guide tube is a member in which a slit capable of clamping the guide tube is formed on a projection projecting out of the needle-housing member.

A twenty-fourth aspect of the present invention is a winged injection needle according to the above-mentioned twenty-third aspect wherein the member capable of clamping the guide tube is provided on the side of the rear end of the needle-housing member, and the slit opens toward the forward end of the needle-housing member.

A twenty-fifth aspect of the present invention is a winged injection needle according to any one of the above-mentioned first to twenty-fourth aspects wherein the guide tube is provided with a liquid drip prevention mechanism.

A twenty-sixth aspect of the present invention is a winged injection needle according to any one of the above-mentioned eleventh to twenty-fifth aspects wherein the hub (b) has on both sides members for preventing the hub (b) from rocking within the lumen of the needle-housing member.

A twenty-seventh aspect of the present invention is a winged injection needle according to any one of the above-mentioned first to twenty-sixth aspects wherein the needle-housing member has on its outer face a finger/thumb hold.

First Type of Winged Injection Needle

To detail more specifically the constitution related to the above-mentioned first type of winged injection needle, the above-mentioned winged injection needle has the following constitution.

A base end (the part on the side opposite to the puncturing part) of a puncture needle made of metal is retained and fixed to a spherical hub, and the base end of the hub (the side opposite to the forward end on which the needle is mounted) communicates with a flexible tube via a linking part. The spherical hub defined here can have a hub middle part formed so as to have the maximum diameter on a cross section in the axial direction of the needle, and two hub side parts that are formed so as to have reduced diameters compared to the middle part, wherein the hub middle part having the largest diameter and the two hub side parts having reduced diameter are connected continuously with a smooth curve. The entire hub may be spherical or either one of the hub ends may be formed so as to be square (rectangular) as hereinafter described.

The position of the spherical hub can be changed by sliding the outer surface thereof along the lumen of a hollow needle-housing member. The needle-housing member has a forward end side for exposing and housing a needle and a base end side for inserting a guide tube therethrough, and is provided with at least two enlargement-constriction units in which an increased diameter part and a reduced diameter part are formed alternately as in the state where there are, going from the forward end side to the base end side, a reduced diameter part (on the forward end side), an increased diameter part (on the forward end side), a reduced diameter part (in the middle), an increased diameter part (on the base end side), and a reduced diameter part (on the base end side). For example, there can be cited one in which three reduced diameter parts and two increased diameter parts are provided.

Figure 1:
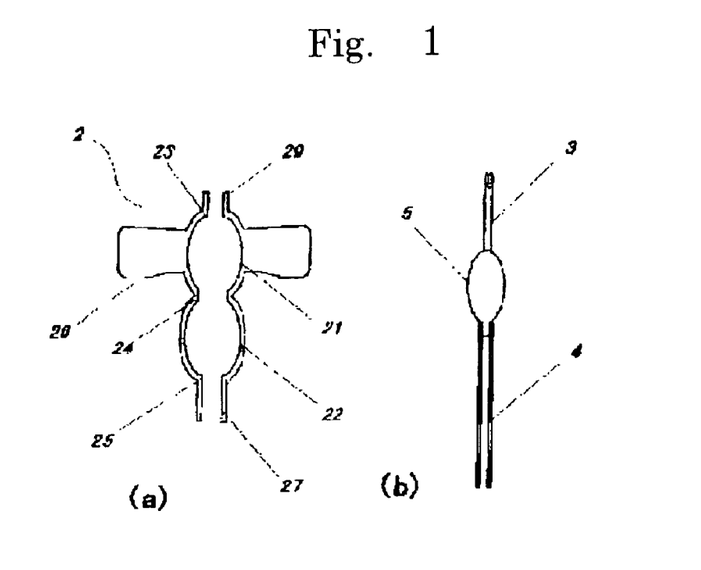
FIG. 1 is a schematic diagram showing one embodiment of the first type of winged injection needle.
 (a) is a diagram showing a needle-housing member.
 (b) is a diagram separately showing a needle and a hub.

With regard to the needle-housing member, a gourd-shaped needle-housing member 2 shown in, for example, FIG. 1 can be specifically cited. Although the entire needle-housing member 2 shown in FIG. 1 forms a gourd shape, it is not always necessary for the whole to have a gourd shape, and it is sufficient for the lumen thereof alone to form a reduced diameter part, an increased diameter part, a reduced diameter part, an increased diameter part, and then a reduced diameter part. The enlargement-constriction unit referred to here means a unit in which an increased diameter part and a reduced diameter part are connected continuously, and these parts can be in any order. With regard to the needle-housing member, at least the lumen thereof is flexible and when it is pressed by the spherical hub it can be distorted so as to expand outwardly. When the pressure is released, the hub lumen is restored to its original shape. Two flexible wings are formed on the outer surface of the needle-housing member.

Second Type of Winged Injection Needle

The second type of winged injection needle of the present invention relates to a winged injection needle that includes at least a needle tube (a) for puncturing, a hub (b) for retaining the base end of the needle tube, a hollow needle-housing member (c) allowing the hub to be displaced by sliding within the lumen of the needle-housing member (c) and allowing the entirety of the needle tube for puncturing and the hub to be housed within the lumen by the displacement, a pair of flexible wings (d) projectingly formed on the left and right outer faces of the hollow needle-housing member (c), and a guide tube (e) joined to the hub (b), wherein the lumen of the hollow needle-housing member (c) is provided with at least two expanded parts (f) spaced by the length of needle exposed via a reduced diameter part, the expanded parts (f) being expanded radially outward and allowing at least one part of the upper part of the hub (b) to be housed therein.

The reduced diameter part in the lumen of the needle-housing member (c) and the hub (b) of the aforementioned winged injection needle are formed in shapes such that the hub (b) can be displaced by sliding within the lumen of the hollow needle-housing member (c), and the hollow needle-housing member (c) is preferably formed from a flexible material.

With regard to the above-mentioned hub (b), its upper part is preferably formed so as to have an arced curved shape in the axial direction having a middle part that is formed so as to have the largest diameter in the axial direction and two side parts formed so as to have gradually reduced diameters relative to the middle part, and its two side faces are preferably formed so as to be straight. However, the hub shape employed in the present invention is not limited by the above-mentioned hub shape as long as the hub (b) can be displaced by sliding within the lumen of the hollow needle-housing member (c) and can be retained and fixed by at least one part of the upper part of the hub (b) being housed within the lumen of the hollow needle-housing member (c).

With regard to the above-mentioned hollow needle-housing member (c), two expanded parts are preferably provided in the vicinity of the forward end thereof and in the vicinity of the terminus thereof, but the positions at which the expanded parts (f) are formed are not necessarily limited to the vicinity of the forward end thereof and the vicinity of the terminus thereof as long as the expanded parts (f) are formed by being spaced via a reduced diameter part.

The shape of the expanded parts (f) is preferably a shape that can house substantially the entire upper part of the above-mentioned hub (b) since the object of the present invention can then be fully achieved, but it may be a shape that can house a part of the hub (b).

The reduced diameter part referred to here denotes a part that has a diameter that is smaller than that of the expanded part, the diameter allowing the hub (b) to slide within the hollow needle-housing member (c) by application of a force to the hub (b) via a guide tube, and it is preferable to use one having a fixed diameter when the ease of sliding of the hub (b) is taken into consideration.

The above-mentioned pair of flexible wings (d) and needle-housing member (c) are preferably formed by molding as one piece using a flexible resin, and the above-mentioned pair of flexible wings (d) can preferably be folded upward and have a flexibility and a length that are sufficient to cover the needle-housing member, and have an immovable attachment member that allows the wings to be immovably attached to each other after they have covered the needle-housing member.

Figure 10:
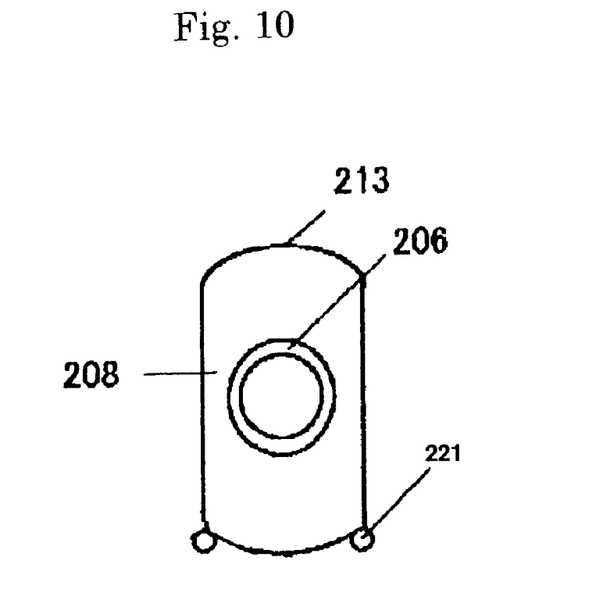
FIG. 10 is a cross section in a plane perpendicular to the axis of the hub shape.

It is also possible to provide, on both sides of the hub (b), members for preventing the hub (b) from rocking within the lumen of the needle-housing member. With regard to such members, for example, as shown in FIG. 10 rocking prevention rails 222 can be provided on a lower part on both sides of the hub (b) in the axial direction of the needle-housing member (c).

With regard to the above-mentioned first and second types of winged injection needle, there are, for example, three methods of assembling a hub and a tube as described below, and there are therefore slight constitutional differences in the shape of the above-mentioned hub. (1) Inserting a tube into the lumen of a hub; (2) fitting a tube to the outer face of a hub end; and (3) setting a needle into a tube, welding it, and further fitting a bridle-shaped hub around the tube.

The above-mentioned assembly method (1) has the advantage that there is no need to increase the dimensions of the hub, and assembly method (2) has the advantages that there is no blockage of the flow path due to adhesive and the tube thickness has little influence on the angle at which the needle is used for puncturing.

Both the above-mentioned first and second types of winged injection needle may be provided with a liquid drip prevention mechanism, a finger/thumb hold, etc., which are described below.

With regard to the liquid drip prevention mechanism, there can be cited a slit provided on the rear end of the needle-housing member. Furthermore, with regard to the liquid drip prevention mechanism, instead of the above-mentioned slit or together with the above-mentioned slit, the flexible tube may be provided with a liquid drip prevention mechanism.

Moreover, with regard to the liquid drip prevention mechanism, there can be cited a member that can clamp a guide tube, the member being separately provided on the rear end of the needle-housing member. Examples of the above-mentioned member include a member having an opening that can clamp the guide tube.

Figure 14:
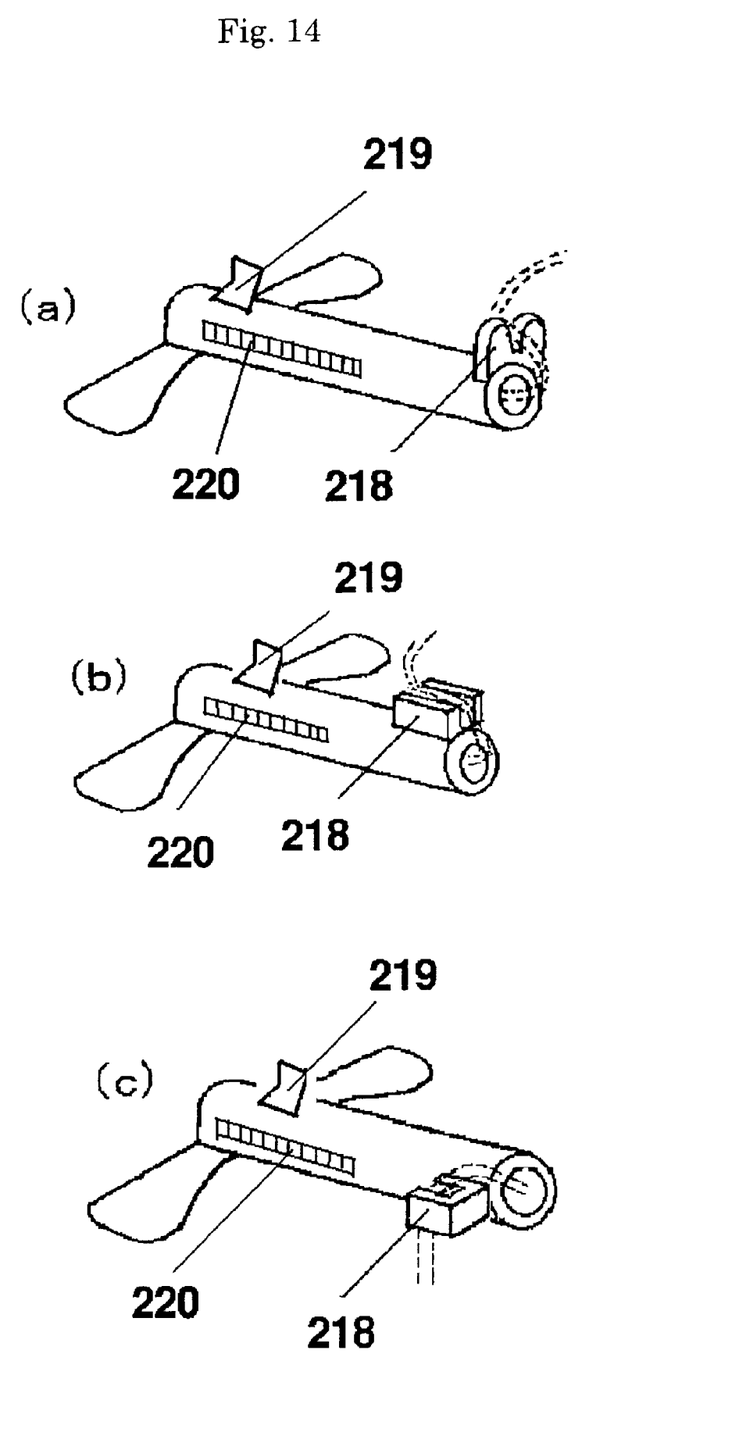
FIG. 14 shows a winged injection needle of the present invention equipped with a liquid drip prevention member 218 of a type other than the above-mentioned slit.
Figure 15:
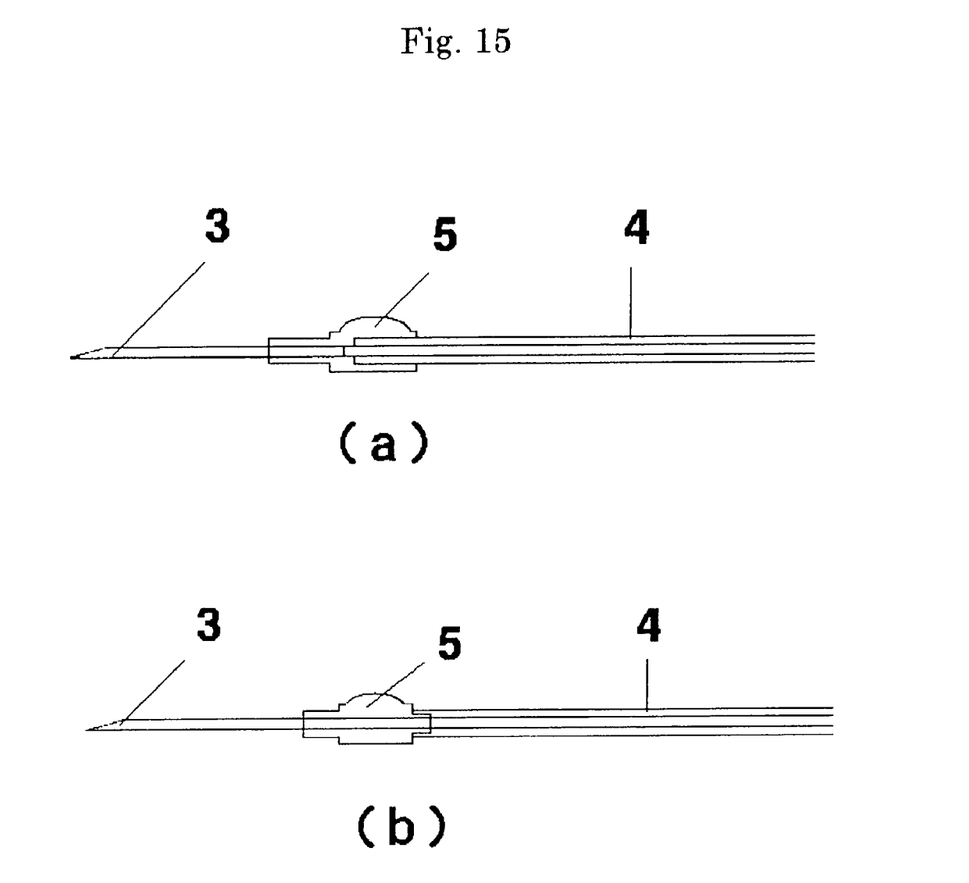
FIG. 15 is a diagram showing a method for assembling the hub and the tube of the winged injection needle;
 (a) corresponds to the above-mentioned (1), and
 (b) corresponds to the above-mentioned (2).

Specific examples of the liquid drip prevention mechanism described above include those shown in FIG. 14 (*a*) to (*c*), and among these it is preferable to employ that shown in (c) in which the member that can clamp a guide tube is provided on the side of the rear end of the needle-housing member and the opening that can clamp the guide tube opens toward the forward end of the needle-housing member since it is easy to make the guide tube latch onto the liquid drip prevention mechanism, thereby allowing a large liquid drip prevention effect to be exhibited.

The finger/thumb hold is provided so that when housing a needle and a needle hub in a needle-housing member by pulling a guide tube the pulling can be carried out easily, and is provided as a projection on the outer face of the needle-housing member.

For example, it corresponds to 219 and 220 shown in FIG. 14.

Furthermore, making the needle-housing member of either the first or second type of winged injection needle of the present invention transparent allows confirmation of the state in which the needle and the needle hub are housed in the needle-housing member, and this effect can be further enhanced by coloring the needle and/or the needle hub.

Embodiments of the first type of winged injection needle are explained below.

Figure 2:
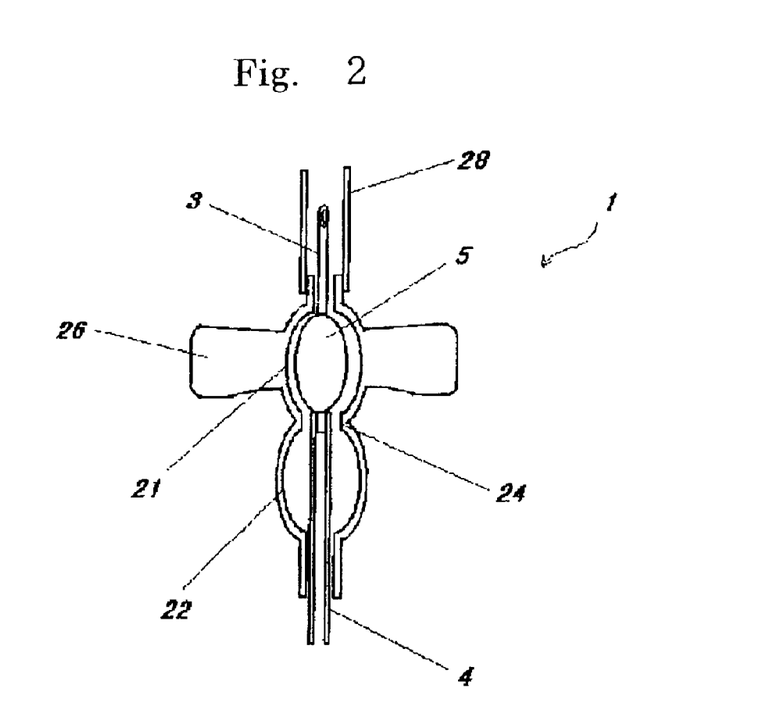
FIG. 2 is a diagram showing a state prior to use in which (a) and (b) are assembled as for actual use.

As shown in FIGS. 1 and 2, a winged injection needle 1 of the present invention includes a needle-housing member 2 and a spherical hub 5 having an injection needle 3 connected to its forward end and a guide tube 4 connected to its base end. The hub 5 has the shape of a rugby ball and an elliptical cross section in the axial direction of the needle as shown in FIG. 2. This allows the hub 5 to move smoothly within the winged needle-housing member 2. The above-mentioned rugby ball-shaped hub is one example, and there are other applicable embodiments.

Figure 4:
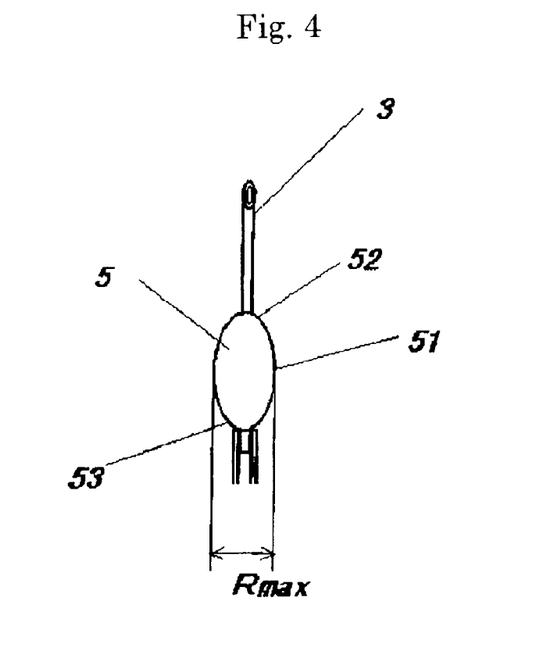
FIG. 4 is a diagram showing the needle and the hub of the above-mentioned figures in more detail.

As shown in FIG. 4, the hub 5 of the present invention has a hub maximum diameter part 51 in the middle, which has a maximum diameter $R_{max}$ in the minor diameter of the elliptical cross section in the axial direction of the needle, and two hub side parts 52 and 53 formed so as to have a diameter that is less than the above diameter. The two side parts refer to curved reduced diameter positions on either side of the maximum increased diameter part 51 and they are not necessarily hub ends.

As shown in FIG. 1, one example of the needle-housing member 2 is a gourd-shaped hollow member having two increased diameter parts 21 and 22 and three reduced diameter parts 23, 24 and 25. In this example, the entire member is formed in a gourd shape, but it is possible for only the lumen to be formed in such a shape. In accordance with the above-mentioned constitution, the hub can be placed in a stable manner in either one of the two increased diameter parts and the spherical hub can be moved smoothly between the increased diameter parts.

With regard to the needle-housing member 2, wings 26 are formed on the outer face thereof so that it is easy to hold when puncturing a patient, and a guide tube insertion inlet 27 is formed on the base end of the housing member 2 in order to insert the guide tube 4 therethrough. Furthermore, formed on the forward end of the housing member 2 through which the needle tube 3 is exposed or housed is a needle cover mounting part 29 on which a needle cover 28 (covering and protecting the needle prior to use) can be mounted. The needle cover mounting part can be formed on the forward end of the hub 5.

In a preferable mode of the present embodiment, the shape and dimensions of the spherical hub and the shapes and dimensions of the increased diameter parts and the reduced diameter parts are devised so that the needle-equipped hub 5 does not move freely within the housing member. For example, in the case of the gourd-shaped housing member 2 as shown in FIG. 1, since it is necessary for the hub 5 to move through the reduced diameter part 24 in the middle, if the inner diameter of the reduced diameter part 24 in the middle is much smaller than that of the maximum diameter part 21 of the hub, it becomes difficult for the hub 5 to pass through the reduced diameter part 24 in the middle, and it becomes difficult for the hub to move within the housing member. On the other hand, if the inner diameter of the reduced diameter part 24 in the middle is larger than that of the maximum diameter part 21 of the hub, the hub 5 can move freely within the housing member and cannot be retained in a stable manner in either of the increased diameter parts 21 or 22, and as a result the needle cannot be retained during puncturing and housing thereby causing poor usability.

Since it is undesirable for the spherical part of the hub to pass through the reduced diameter part 23 on the forward end side, the inner diameter of the reduced diameter part 23 on the forward end side can be large enough for the needle tube 3 to pass through. It is therefore preferable for the inner diameter of the reduced diameter part 23 on the forward end side to be smaller than that of the reduced diameter part 24 in the middle. The reduced diameter part 25 on the base end side preferably has an inner diameter that is larger than that of the reduced diameter part 23 on the forward end side, since it is expected that there will be cases where the spherical part of the hub 5 is inserted or removed through the reduced diameter part 25 on the base end side during production or after use. Other than during production, since it is expected that there will not be many cases in which the hub 5 is moved through the reduced diameter part 25 on the base end side (e.g. a case in which the needle and the hub are removed from the needle-housing member 2 and separated during disposal), the inner diameter of the reduced diameter part 25 on the base end side is desirably the same as or smaller than that of the reduced diameter part 24 in the middle. For the above-mentioned reasons, the inner diameter of the reduced diameter part 24 in the middle is preferably larger than the inner diameters of the reduced diameter part 23 on the forward end side and the reduced diameter part 25 on the base end side. It is more preferable that the inner diameter of the reduced diameter part 25 on the base end side is smaller than that of the reduced diameter part 24 in the middle, and the inner diameter of the reduced diameter part 25 on the base end side is larger than that of the reduced diameter part 23 on the forward end side.

Figure 5:
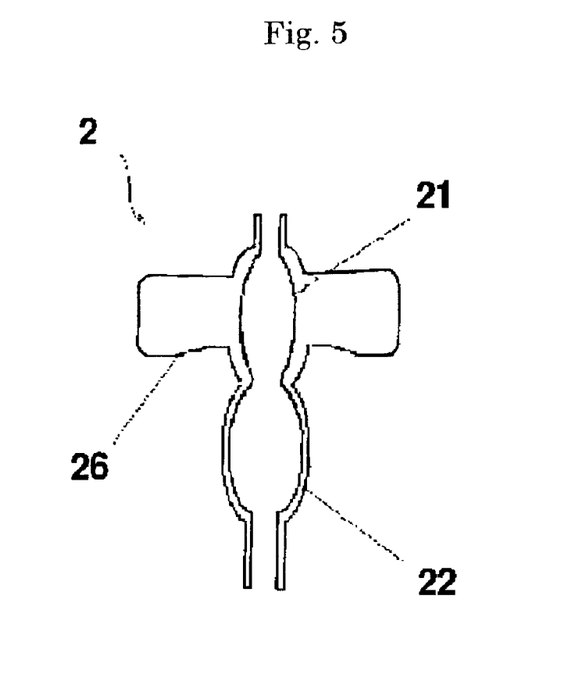
FIG. 5 is a schematic diagram showing another embodiment of the first type of needle-housing member.

As shown in FIG. 5, since it is necessary to securely retain the hub 5 in the housing member 2, it is preferable that, among the aforementioned two increased diameter parts 21 and 22, the maximum inner diameter of the increased diameter part 21 on the forward end side is smaller than the maximum inner diameter of the increased diameter part 22 on the base end side. The reason therefor is to prevent the needle tube 3 from rocking during needle puncture, and it can be retained more reliably if the maximum inner diameter of the increased diameter part 21 on the forward end side in which the hub 5 is positioned while puncturing is smaller than that of the increased diameter part 22 on the base end side in which the hub is positioned when pulling back the needle.

For the same reasons, it is preferable for the increased diameter part 21 on the forward end side and the spherical hub 5 to have similar shapes so that no gap is formed between the increased diameter part 21 on the forward end side and the hub when the hub 5 is positioned in the increased diameter part 21 on the forward end side. In cases where it is difficult to make the overall shapes similar, it is also possible to make parts of their shapes similar including, for example, the parts that are in contact with each other and the vicinities thereof. It is also possible to retain the hub in the increased diameter parts by means of a design in which the dimensions of the parts that are in contact with each other are substantially the same. For example, making the maximum inner diameter of the increased diameter part 21 on the forward end side the same as or slightly smaller than the maximum diameter $R_{max}$ of the hub can put the hub 5 in close contact with the increased diameter part 21 and securely retain it within the housing member.

The sites on the needle-housing member where the wings are formed are not particularly limited, but since operating is easier if the puncturing part and the sites (wings) to be held are closer, it is desirable for the wings 26 to be formed on the outer face of the increased diameter part 21 on the forward end side.

Figure 6:
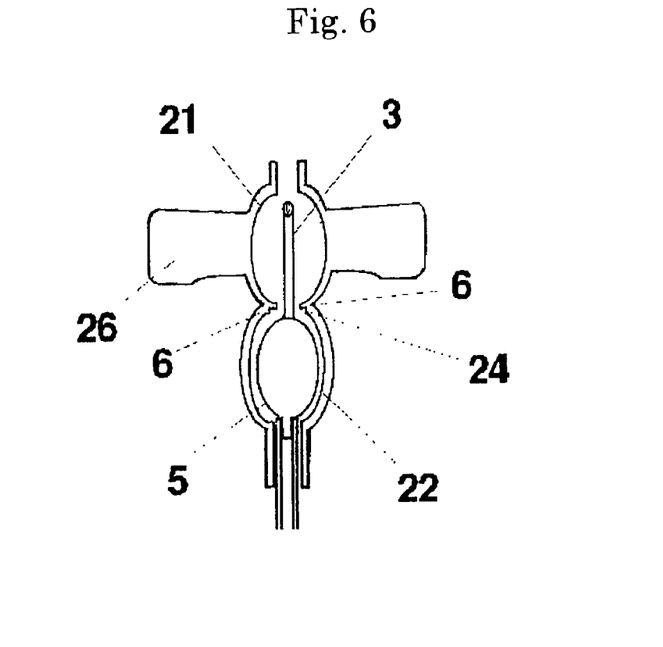
FIG. 6 is a schematic diagram showing yet another embodiment of the first type of winged injection needle.

In order to avoid erroneous reuse of a needle once it has been housed within a housing member, non-return means, such as a check valve 6, may be formed. For example, forming a check valve 6 shown in FIG. 6 in the reduced diameter part 24 in the middle or in the vicinity thereof prevents the hub 5 that has been housed in the increased diameter part 22 on the base end side from returning to the increased diameter part 21 on the forward end side.

In order to prevent blood, etc. from dripping from the needle tube housed within the housing member, it is preferable to provide closure means in the reduced diameter part 23 on the forward end side. For example, there may be a construction such that the inner faces of the reduced diameter part 23 on the forward end side can engage (latch) with each other and close by pressure, or the design may be such that the needle cover mounting part 29 can be bent and latched.

Figure 7:
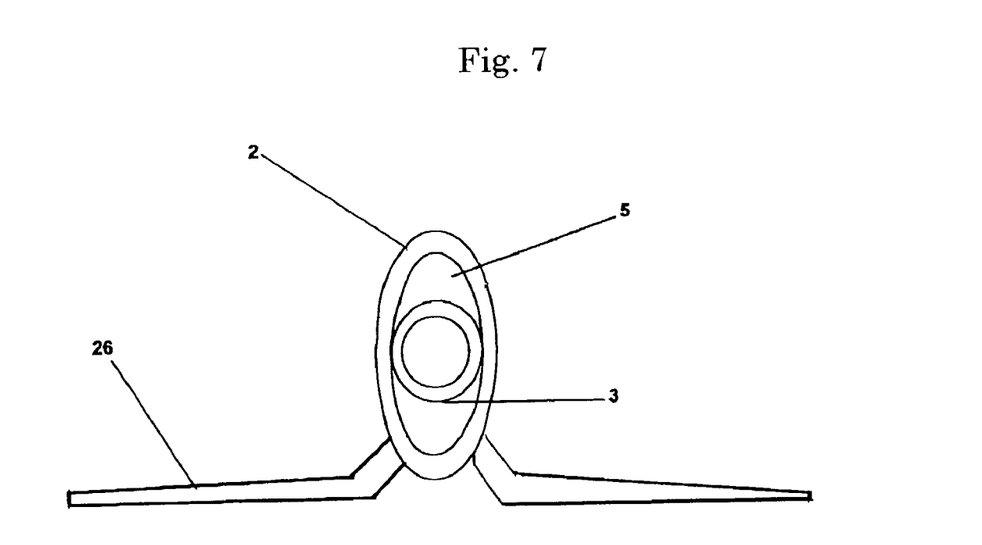
FIG. 7 is a schematic diagram showing a cross section perpendicular to the axial direction of the needle of FIG. 6.

In order to prevent the hub 5 from freely rotating within the lumen of the needle-housing member, the cross section of the hub that is perpendicular to the needle axis is formed so as to be an ellipse or a flattened circle, and the cross section of the lumen of the needle-housing member that is perpendicular to the needle axis is similarly formed so as to be an ellipse or a flattened circle. FIG. 7 shows a brief sketch thereof. In FIG. 7 the hub and the needle-housing member have vertically oriented elliptical shapes, and it is also possible for them to be rotated by 90 degrees to have horizontally oriented elliptical shapes. In accordance with the above-mentioned constitution, the direction of the blade face of the needle can be controlled so as to be aligned with the positions where the wings are formed, and even if the hub is moved within the needle-housing member 2, the blade face will not be displaced relative to the positions of the wings.

Figure 3:
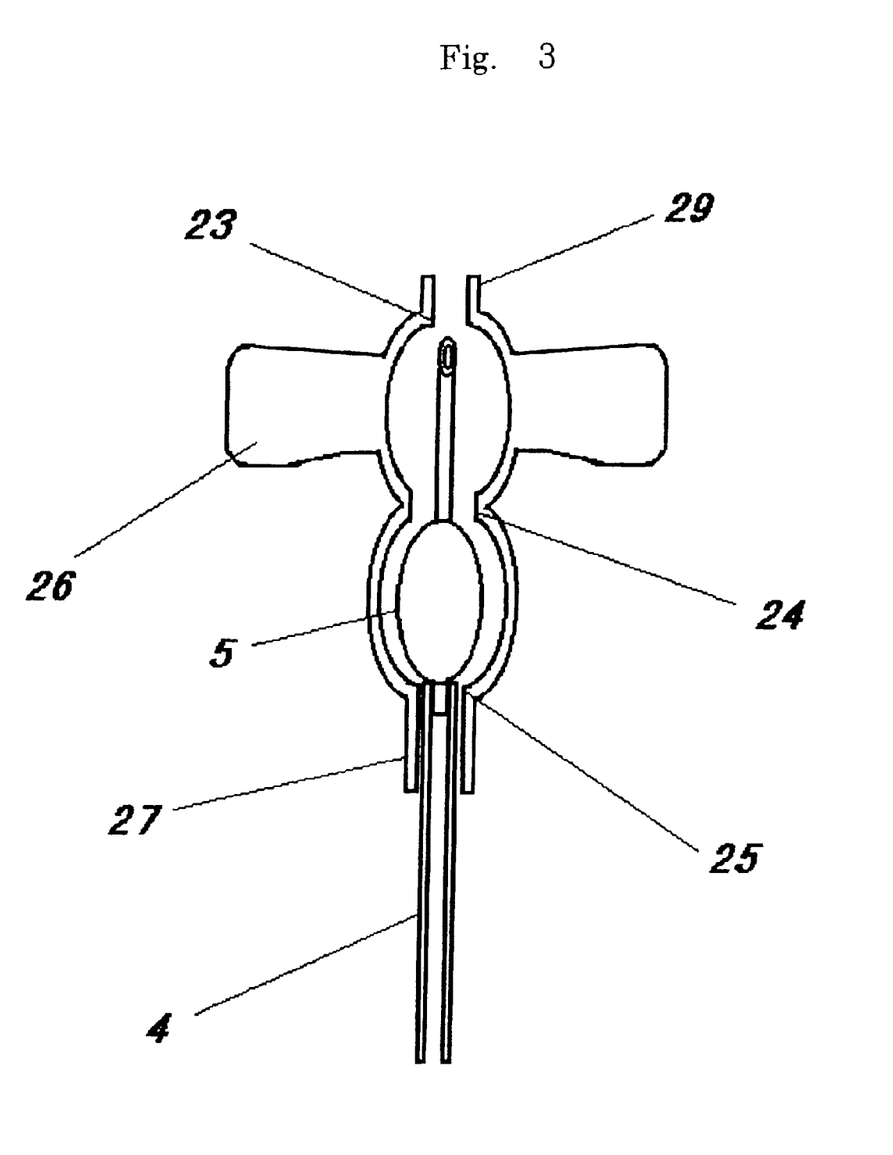
FIG. 3 is a diagram showing a state after the use of FIG. 2.

Next, a brief explanation is given of a method for using one example of the above-mentioned first type of winged injection needle of the present invention. In an unused state, the winged injection needle of the present example is equipped with a needle cover 28 (FIG. 2). The needle cover is removed immediately before puncturing a patient with the injection needle, and the needle tube 3 punctures the affected area while the wings 26 are gripped with the fingers/thumb. At this point, the wings may be fixed to the affected area by means of adhesive tape so that the injection needle does not come out. After the use is finished, while pressing the wings 5 or the needle-housing member 2 with one hand so as to prevent movement thereof, the operator pulls the guide tube 4 to the rear (toward the direction opposite to the puncture site) with the remaining hand. As a result, only the needle and the hub move within the lumen of the needle-housing member 2 and the hub 5 is housed in the increased diameter part 22 on the base end side from the increased diameter part 21 on the forward end side (FIG. 3). Accompanying this, the needle tube 3 comes out of the punctured part. Since the punctured part as well as the housing member are pressed by the operator's hand at this time, there is little bleeding.

Removal of the needle from the punctured part can be carried out using a method other than the above-mentioned method. For example, after the needle-housing member 2 has been removed together with the needle and hub by gripping the wings, the needle can be housed in the lumen of the housing member. The needle and hub that, without exposure, have been housed within the needle-housing member by the above-mentioned method can be disposed of separately by removing the needle (hub) from the needle-housing member by further pulling the guide tube 4 while holding the needle-housing member 2.

BRIEF DESCRIPTION OF DRAWINGS

In FIG. 14, the constituent features of the present invention other than the wings are omitted.

DESCRIPTION OF THE PREFERRED EMBODIMENTS

Figure 8:
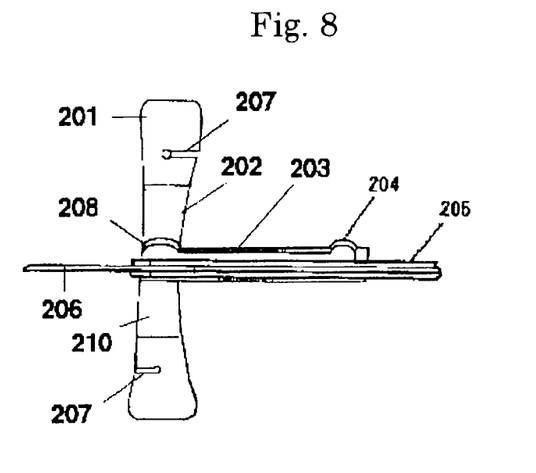
FIG. 8 is a diagram of the second type of winged injection needle showing a state before housing a needle tube and a hub in a needle-housing member.
Figure 9:
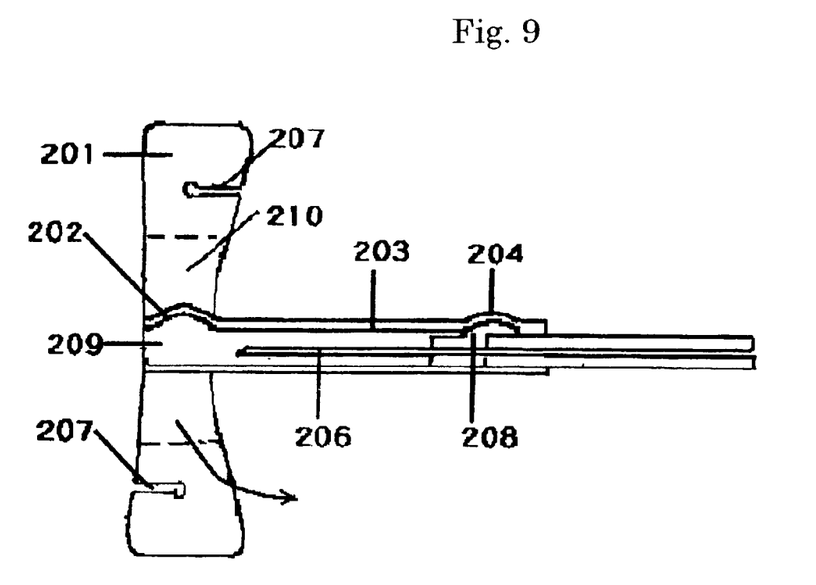
FIG. 9 is a diagram showing a state after housing the needle tube and the hub in the needle-housing member in FIG. 8.

As shown in FIGS. 8 and 9, the winged injection needle of the present embodiment is a winged injection needle that includes a needle tube 206 for puncturing, a hub 208 for retaining the base end of the needle tube, a hollow needle-housing member 2 having a lumen 209 in which the entirety of the needle tube 206 for puncturing and the hub 208 can be housed by sliding the hub 208, a pair of flexible wings 201 projectingly formed on the left and right outer faces of the hollow needle-housing member, and a flexible tube 205 on the hub 208; the lumen 209 of the hollow needle-housing member is provided, via a reduced diameter part 203, with expanded parts 202 and 204 that expand radially outward in a shape that complementarily corresponds to (substantially coincides with) the whole upper part of the hub 8 (second type of winged injection needle).

Preferably provided in the flexible tube 205 and/or the hollow needle-housing member 2 is a member for preventing liquid drips from the flexible tube 205. With regard to the member for preventing liquid drips, the members for preventing liquid drips shown in FIG. 14 (a) to (c) are particularly preferred.

With regard to the materials from which are formed the housing member 2 and the flexible wings 201 that are formed as one piece with the housing member 209, for example, a polyolefin such as polyethylene or polypropylene, an elastomer, etc. can be cited. The material for the housing member is desirably a flexible material so that, when the hub is housed in the expanded part, the hub can be held in the lumen of the needle-housing member with a moderate strength, and when the hub is moved within the housing member (through a reduced diameter part), a moderate slidability can be exhibited. With regard to the material from which the above-mentioned hub 208 is formed, a comparatively hard material is desirable so that it can be held with a moderate strength by the above-mentioned flexible housing member and can move. Examples of the material for the hub include polycarbonate and hard vinyl chloride resins, but it is not particularly limited by these materials as long as the object of the present invention can be achieved.

Although it is not illustrated, prior to use the needle tube for puncturing may be protected with a protecting cover as in the above-mentioned first type of winged injection needle.

As shown in FIG. 10 (cross section in a plane perpendicular to the hub shaft), the hub shaft of the needle of the present embodiment is formed in a manner in which the upper face 213 has an arc shape in the axial direction, both side faces have a straight shape, and the lower face has a flat shape or a (shallow) arc shape in the axial direction. The arc shape on the upper side is formed in an arced curved shape in the axial direction, the arced curved shape comprising a middle part formed so as to have a maximum diameter in the axial direction and two side parts formed so as to have diameters that reduce gradually from the above-mentioned diameter. The hub 208 can therefore be latched advantageously within the lumen 209 of the above-mentioned hollow needle-housing member, and the straight-shaped cut-offs on the two sides make it difficult for the hub to rotate within the protector, thereby advantageously controlling the injection needle in a fixed direction.

Furthermore, since the lower side of the outer surface of the above-mentioned hollow needle-housing member often makes contact with the skin, it is preferably flat or has a small curvature, and the lower face of the hub 208 is also preferably flat or an arc shape having a small curvature. Moreover, the hub 208 whose lower face is flat or has an arc shape having a small curvature has excellent movability (slidability) in the reduced diameter part 203 of the lumen of the hollow needle-housing member.

In the case where a lower part of the aforementioned hub 208 has an arc shape, in order to prevent the hub from rocking within the lumen of the needle-housing member, a rocking prevention member such as, for example, a rocking prevention rail 222 shown in FIG. 10 may be formed in the direction of the hub shaft.

By providing the expanded parts 202 and 204 on the forward end and the rear end of the above-mentioned hollow needle-housing member via the reduced diameter part 203 of the needle-housing member, the hub shaft can be reliably latched, when housing the needle the possibility of reprojecting the needle part can be reduced, and when exposing the needle an undesirable retreat of the needle while puncturing can be prevented.

The number of the aforementioned expanded parts is not limited to two, and it is also possible to provide a plurality thereof such as two or more. The shape of the expanded part is not particularly limited as long as it is capable of functioning for both latching and moving the hub shaft in concert with the reduced diameter part that is formed between the expanded parts, but when taking the function of latching the hub shaft into consideration, it preferably has a shape that can complementarily coincide with (correspond to) the shape of the upper face of the aforementioned hub shaft, and can house at least one part, and preferably the whole, of the upper face of the hub shaft.

Figure 11:
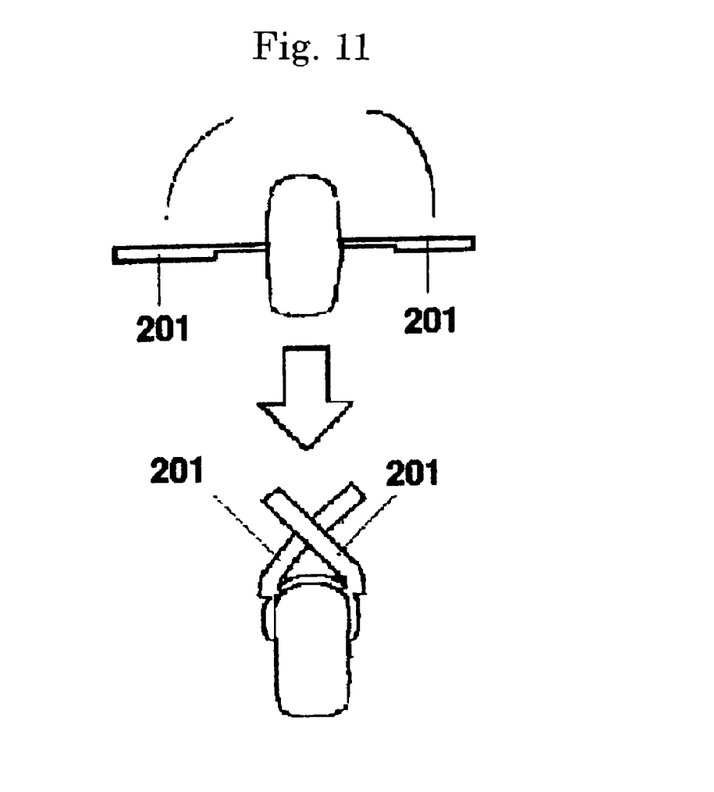
FIG. 11 is an explanatory diagram showing an operation in which the wings are each folded upward, and by means of slits provided on each of the wings the needle-housing member is wrapped, thereby immovably attaching each of the wings 201, 201.
Figure 12:
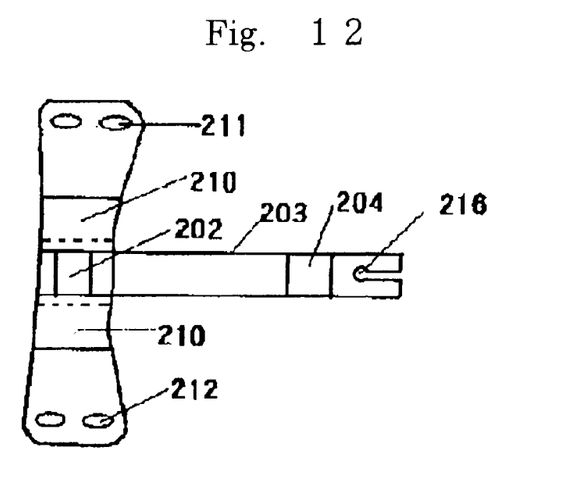
FIG. 12 is a diagram showing a winged needle having a slit on the rear end of the needle-housing member as a liquid drip prevention mechanism shown in a third embodiment.
Figure 13:
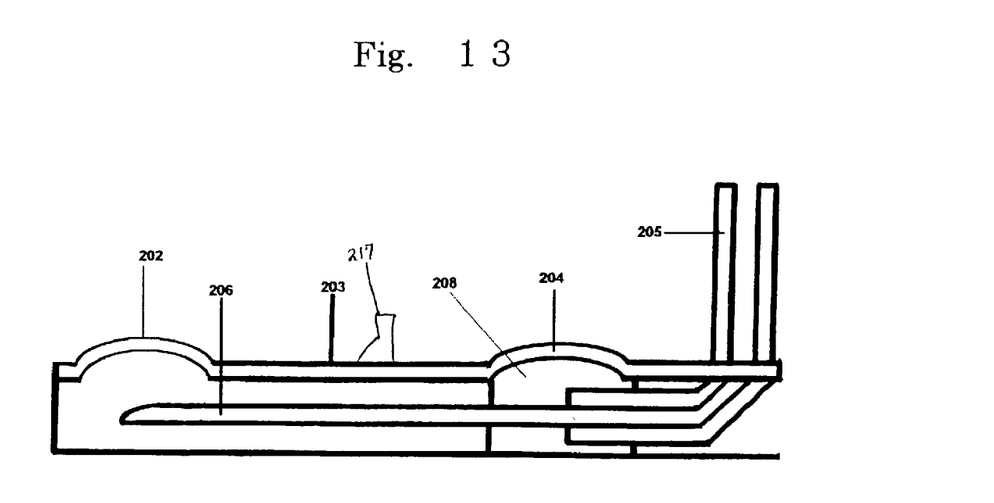
FIG. 13 is a diagram showing a state in which a finger/thumb hold 217 that is used for pulling a guide tube is formed on the surface of the needle-housing member of FIG. 12, and the tube is clamped by the liquid drip prevention member or liquid trap slit 216 in the rear end of the needle-housing member, thereby preventing liquid from dripping.

The pair of flexible wings 201, 201 have sufficient flexibility and length so that the needle-housing member (C) can be easily fixed and retained on a patient's skin. However, the flexibility and length of the wings are not particularly limited and may be the flexibility and length of an ordinarily used wing. Furthermore, the thickness of a part 210 of each of the wings that is in the vicinity of the needle-housing member is comparatively thin in comparison with the thickness of the other wing parts, thereby making it easy to hold the wings and bend them.

INDUSTRIAL APPLICABILITY

In accordance with the present invention, there is provided a winged injection needle equipped with erroneous puncture prevention means that satisfies the following three conditions:
(1) it allows the injection needle to be more safely and easily housed after use;
(2) it has a simple structure, ease of handling, and ease of production at low cost; and
(3) it can be safely disposed of.

The invention has been described with particular emphasis on the preferred embodiments, but variations and modifications within the spirit and scope of the invention may occur to those skilled in the art to which the invention pertains.

The invention claimed is:

1. A winged injection needle comprising:
a needle tube for puncturing having a lumen, a base end, a terminus, a base end side and a forward end side opposite said base end side,
a hub for retaining the base end of the needle tube,
a hollow needle-housing member having left and right outer faces,
a pair of flexible wings projectingly formed on the left and right outer faces of the hollow needle-housing member, and
a guide tube joined to the hub, and
wherein:
(1) the hub is formed to have an arced curved shape including an upper part in the axial direction, wherein said upper part is formed from a middle part forming a maximum diameter in the axial direction and two side parts forming diameters gradually reduced from the maximum diameter,
(2) the hollow needle-housing member is formed from a flexible material;
(3) the hollow-needle-housing member has at least two expanded parts each formed with an inner surface and an outer surface corresponding to the inner surface expanding radially outward, wherein the expanded parts can house therein at least one part of an upper part of the hub; and
(4) the two expanded parts are spaced via a reduced diameter part, wherein the reduced diameter part has a reduced inner and outer diameter.

2. The winged injection needle according to claim 1 wherein the rear end of the needle-housing member further includes a liquid drip prevention mechanism.

3. The winged injection needle according to claim 2 wherein the liquid drip prevention mechanism is a member separately provided on the rear end of the needle-housing member and capable of clamping the guide tube.

4. The winged injection needle according to claim 3 wherein the member capable of clamping the guide tube is a member having an opening capable of clamping the guide tube.

5. The winged injection needle according to claim 4 wherein the member capable of clamping the guide tube is provided on the side of the rear end of the needle-housing member, and the opening opens toward the forward end of the needle-housing member.

6. The winged injection needle according to claim 2 wherein the liquid drip prevention mechanism is a slit provided in the rear end of the needle-housing member.

7. The winged injection needle according to claim 1 wherein said hub has two side faces and both side faces of the hub have a straight shape.

8. The winged injection needle according to claim 1 wherein two of the expanded parts are provided in the vicinity of the forward end side and in the vicinity of the terminus of the hollow needle-housing member.

9. The winged injection needle according to claim 1 wherein the expanded parts have a shape housing substantially the entire upper part of the hub.

10. The winged injection needle according to claim 1 wherein the pair of flexible wings are upwardly foldable and have a flexibility and a length sufficient to cover the needle-housing member, and have an immovable attachment member allowing the wings to be immovably attached to each other after covering the needle-housing member.

11. The winged injection needle according to claim 1 wherein the guide tube has a liquid drip prevention mechanism.

12. The winged injection needle according to claim 1 wherein the pair of flexible wings and the needle-housing member are formed by molding as one piece using a flexible resin.

13. The winged injection needle according to claim 1 wherein the rear end of the needle-housing member further includes a liquid drip prevention mechanism.

* * * * *